US00PP25958P2

(12) United States Plant Patent
Alamillo

(10) Patent No.: US PP25,958 P2
(45) Date of Patent: Sep. 29, 2015

(54) ***HOSTA* PLANT NAMED 'MONLISA'**

(50) Latin Name: *Hosta tardiana*
Varietal Denomination: MonLisa

(71) Applicant: Andres Alamillo, Sherwood, OR (US)

(72) Inventor: Andres Alamillo, Sherwood, OR (US)

(73) Assignee: Monrovia Nursery Company, Azusa, CA (US)

( * ) Notice: Subject to any disclaimer, the term of this patent is extended or adjusted under 35 U.S.C. 154(b) by 181 days.

(21) Appl. No.: 13/987,983

(22) Filed: Sep. 20, 2013

(51) Int. Cl.
*A01H 5/12* (2006.01)

(52) U.S. Cl.
USPC ..... Plt./353

(58) Field of Classification Search
USPC ..... Plt./353
See application file for complete search history.

*Primary Examiner* — June Hwu
(74) *Attorney, Agent, or Firm* — C. A. Whealy

(57) ABSTRACT

A new and distinct cultivar of *Hosta* plant named 'MonLisa', characterized by its medium-sized plant with uniformly mounding plant habit; vigorous growth habit; medium bluish green-colored leaves with wide creamy white-colored borders; pale lavender-colored flowers positioned on strong peduncles; and good garden performance.

1 Drawing Sheet

Botanical designation: *Hosta tardiana.*
Cultivar denomination: 'MONLISA'.

BACKGROUND OF THE INVENTION

The present invention relates to a new and distinct cultivar of *Hosta* plant, botanically known as *Hosta tardiana* and hereinafter referred to by the name 'MonLisa'.

The new *Hosta* plant is a naturally-occurring whole plant mutation of the *Hosta tardiana* 'Halcyon', not patented. The new *Hosta* plant was discovered and selected by the Inventor in a controlled nursery environment in Dayton, Oreg. in 2010.

Asexual reproduction of the new *Hosta* plant by tissue culture in a controlled environment in Dayton, Oreg. since 2010 has shown that the unique features of this new *Hosta* plant are stable and reproduced true to type in successive generations.

SUMMARY OF THE INVENTION

Plants of the new *Hosta* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'MonLisa'. These characteristics in combination distinguish 'MonLisa' as a new and distinct *Hosta* plant:

1. Medium-sized plant with uniformly mounding plant habit.
2. Vigorous growth habit.
3. Medium bluish green-colored leaves with wide creamy white-colored borders.
4. Pale lavender-colored flowers positioned on strong peduncles.
5. Good garden performance.

Plants of the new *Hosta* differ primarily from plants of the parent, 'Halcyon', primarily in leaf color as plants of 'Halcyon' do not have variegated leaves. In addition, plants of the new *Hosta* and 'Halcyon' differ in flower color as plants of 'Halcyon' have white-colored flowers.

Plants of the new *Hosta* can be compared to plants of 'Frosted Jade', not patented. Plants of the new *Hosta* and 'Frosted Jade' differ primarily in the following characteristics:

1. Plants of the new *Hosta* are more compact than plants of 'Frosted Jade'.
2. Plants of the new *Hosta* and 'Frosted Jade' differ in leaf color as plants of 'Frosted Jade' have sage green-colored leaves with narrow white-colored borders.
3. Plants of the new *Hosta* and 'Frosted Jade' differ in flower color as plants of 'Frosted Jade' have white-colored flowers.

BRIEF DESCRIPTION OF THE PHOTOGRAPHS

The accompanying colored photographs illustrate the overall appearance of the new *Hosta* plant showing the colors as true as it is reasonably possible to obtain in colored reproductions of this type. Colors in the photographs may differ slightly from the color values cited in the detailed botanical description which accurately describe the colors of the new *Hosta* plant.

The photograph at the right side of the sheet comprises a side perspective view of a typical flowering plant of 'MonLisa' grown in a container.

The photograph at the left side of the sheet is a close-up view of typical inflorescences of 'MonLisa'.

DETAILED BOTANICAL DESCRIPTION

The aforementioned photographs and following observations, measurements and values describe plants grown during the summer in two-gallon containers in an outdoor nursery in Dayton, Oreg. and under cultural practices typical of commercial production. During the production of the plants, day temperatures averaged 17° C. and night temperatures averaged 3° C. Plants were three years old when the photographs and description were taken. In the following description, color references are made to The Royal Horticultural Society Colour Chart, 2007 Edition, except where general terms of ordinary dictionary significance are used.

Botanical classification: *Hosta tardiana* 'MonLisa'.

Parentage: Naturally-occurring whole plant mutation of *Hosta tardiana* 'Halcyon', not patented.

Propagation:

*Type.*—By tissue culture.

*Time to produce a rooted young plant, summer.*—About one month at soil temperatures of 16° C. to 24° C.

*Root description.*—Medium in thickness, fleshy; white in color.

*Rooting habit.*—Freely branching; medium density.

Plant description:

*Plant form and growth habit.*—Herbaceous flowering perennial plant; medium-sized plant with uniformly mounding plant habit; vigorous growth habit; flowering stems and leaves basal.

*Growth rate.*—About one year is required to produce fully-grown plants in one-gallon containers.

*Plant height, soil level to top of foliar plane.*—About 29 cm.

*Plant height, soil level to top of inflorescences.*—About 56 cm.

*Plant width* (*spread*).—About 68 cm.

Leaf description:

*Arrangement.*—Leaves basal, simple.

*Length.*—About 14 cm.

*Width.*—About 8 cm.

*Shape.*—Lanceolate.

*Apex.*—Acuminate.

*Base.*—Attenuate.

*Margin.*—Entire.

*Texture, upper and lower surfaces.*—Smooth, glabrous; prominent venation.

*Venation pattern.*—Parallel.

*Color.*—Developing leaves, upper surface: Center, close to 147B; towards the margins, close to 157B. Developing leaves, lower surface: Close to 146B to 146C. Fully expanded leaves, upper surface: Center, close to N189A; transition color, closer to 190D; towards the margins, close to 157D; venation, close to N189B. Fully expanded leaves, lower surface: Center, close to 188A; transition color, close to 191B; towards the margins, close to NN155D; venation, close to 188A.

*Petioles.*—Length: About 25 cm. Diameter: About 1 cm; at the base, close to 1.9 cm. Texture, upper and lower surfaces: Smooth, glabrous. Color, upper surface: Close to 191A; margins, close to 157C. Color, lower surface: Close to 147C; towards the base, scattered flecks, close to 185B.

Flower description:

*Flower type and flowering habit.*—Single campanulate flowers with fused perianth arranged on short terminal racemes; flowers face outwardly; freely flowering habit with about 45 flowers develop per raceme over the flowering period.

*Fragrance.*—None detected.

*Natural flowering season.*—Plants flower from late June to mid-July in Oregon.

*Postproduction longevity.*—Flowers last about two to three days on the plant; flowers not persistent.

*Inflorescence height.*—About 6.5 cm to 7 cm.

*Inflorescence diameter.*—About 8.2 cm.

*Flower buds.*—Height: About 3.6 cm. Diameter: Towards the apex, about 1.2 cm; tube, about 3 mm. Shape: Oblong. Color: Close to 92D.

*Flower diameter.*—About 3 cm.

*Flower depth, base to tepal tips.*—About 4.5 cm.

*Perianth.*—Arrangement: Three interior tepals arranged in a single whorl surrounded by an outer whorl of three exterior tepals; tepals fused at the base into a short tube. Tepal lobe length: About 2.6 cm. Tepal lobe width: About 1.2 cm. Tepal tube length: About 1.3 cm. Tepal tube diameter: About 3 mm. Tepal lobe shape: Elliptical. Tepal apex: Acute. Tepal margin: Entire. Tepal texture, upper and lower surfaces: Smooth, glabrous. Tepal color: Developing tepals, upper surface: Close to 91B to 91C. Developing tepals, lower surface: Close to 91C to 91D. Fully expanded tepals, upper surface: Close to 91D; central stripe, close to 91C; color becoming closer to 92D with development. Fully expanded tepals, lower surface: Close to 91C.

*Flower bracts.*—Quantity: One per flower at the base of the pedicel. Length: About 1.1 cm. Width: About 2.5 cm. Shape: Ovate. Apex: Acute. Margin: Entire. Texture, upper and lower surfaces: Smooth, glabrous. Color, upper and lower surfaces: Close to 148C.

*Peduncles* (*scapes*).—Length: About 42 cm. Diameter: About 7 mm. Aspect: Erect to slightly outwardly. Strength: Strong. Texture: Smooth, glabrous. Color: Close to 148B; tiny flecks, close to 183D.

*Pedicels.*—Length: About 6 mm. Diameter: About 2 mm. Angle: Initially upright and with development, about 90° from peduncle axis. Strength: Strong. Texture: Smooth, glabrous. Color: Close to 157C.

*Reproductive organs.*—Stamens: Quantity per flower: Typically six; anthers dorsifixed. Filament length: About 4.2 cm. Filament color: Close to 192D. Anther shape: Narrowly oblong. Anther length: About 4 mm. Anther color: Close to 199C. Pollen amount: Moderate. Pollen color: Close to 163B. Pistils: Quantity per flower: One. Pistil length: About 5.4 cm. Style length: About 4.6 cm. Style color: Close to 196B. Stigma shape: Round. Stigma color: Close to 196B. Ovary color: Close to 194C.

*Seeds and fruits.*—Seed and fruit development have not been observed on plants of the new *Hosta.*

Disease & pest resistance: Plants of the new *Hosta* have not been noted to be resistant to pathogens and pests common to *Hosta.*

Garden performance: Plants of the new *Hosta* have been observed to have good garden performance and to tolerate rain, wind and temperatures ranging from −25° C. to 30C. Plants of the new *Hosta* are suitable for USDA Hardiness Zones 4 through 8.

It is claimed:

1. A new and distinct *Hosta* plant named 'MonLisa' as illustrated and described.

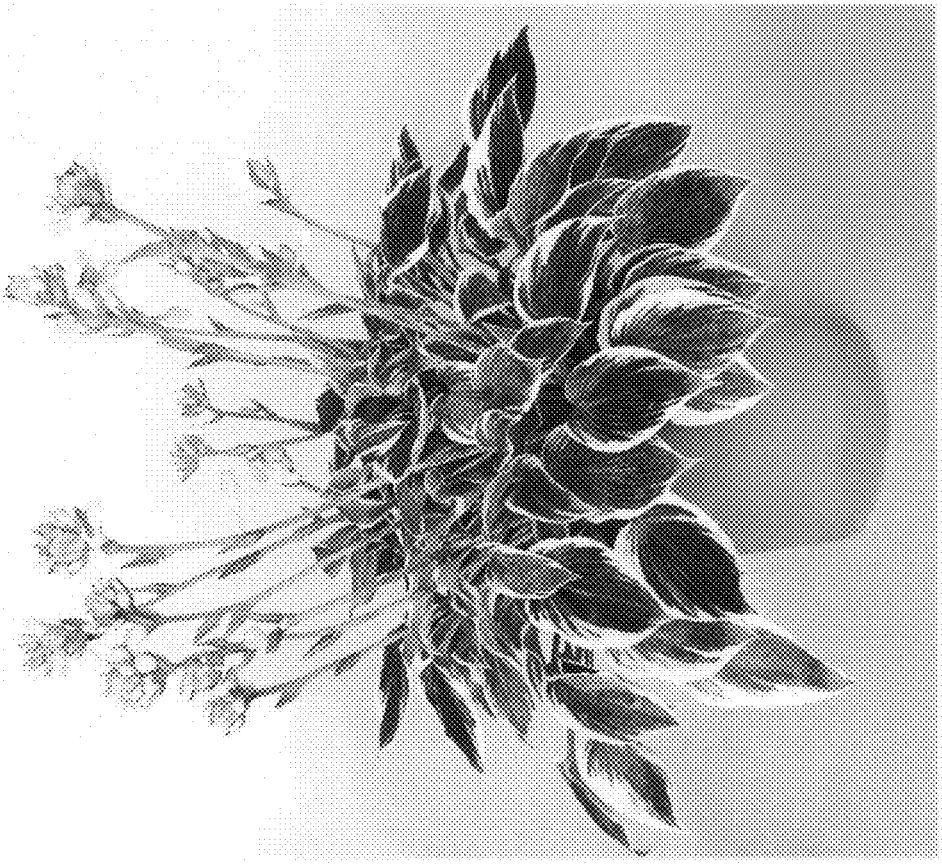
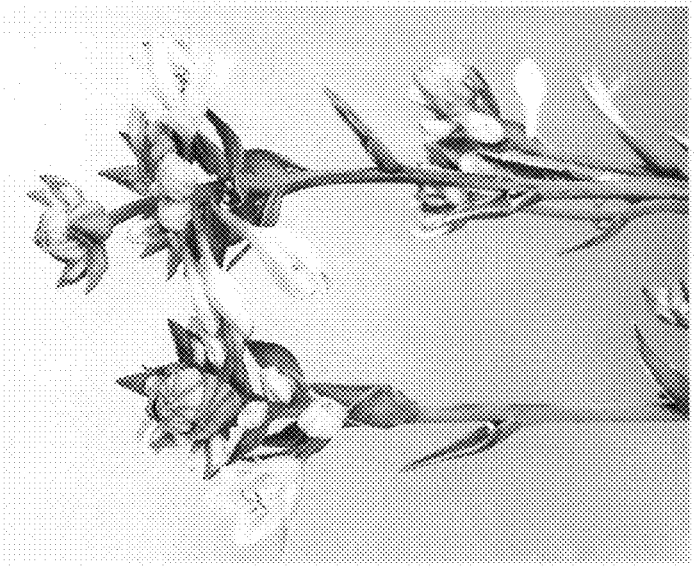

* * * * *